United States Patent [19]

Bruck

[11] Patent Number: 4,559,054
[45] Date of Patent: Dec. 17, 1985

[54] RATE-CONTROLLED DRUG RELEASE SYSTEM

[75] Inventor: Stephen D. Bruck, Rockville, Md.

[73] Assignee: Research Corporation, New York, N.Y.

[21] Appl. No.: 639,277

[22] Filed: Aug. 9, 1984

[51] Int. Cl.⁴ ............................................. A61M 31/00
[52] U.S. Cl. ...................... 604/892; 424/19; 424/21; 424/DIG. 7; 204/192 R
[58] Field of Search ...................... 424/DIG. 7, 16, 19, 424/21; 604/890, 892; 204/192 R

[56] References Cited

U.S. PATENT DOCUMENTS 3,948,254  4/1976  Zaffaroni ............................ 604/892
3,993,072  11/1976  Zaffaroni ............................. 424/19
4,215,691  8/1980  Wong ................................. 604/892
4,235,988  11/1980  Fildes ................................ 424/19
4,377,010  3/1983  Fydelor et al. ................... 210/500.1

Primary Examiner—Andrew H. Metz
Assistant Examiner—Terryence Chapman
Attorney, Agent, or Firm—Scully, Scott, Murphy and Presser

[57] ABSTRACT

A drug release device employing a block copolymer of poly(ether-urethane)/poly(dimethyl siloxane) is useful for dispensing lipophilic drugs at a high controlled rate for prolonged periods of time. The initial "burst effect" of drug release experienced with prior drug release devices is eliminated or at least substantially reduced with these devices.

16 Claims, 6 Drawing Figures

RATE-CONTROLLED DRUG RELEASE SYSTEM

BACKGROUND OF THE INVENTION

1. Field of the Invention

This invention relates to the controlled release of drugs. More particularly, this invention relates to polymeric devices for releasing a drug at a controlled rate over a prolonged period of time. This invention especially relates to improvements in rate-controlled drug release systems through the use of a particular polymeric material.

2. Description of the Prior Art

Polymeric devices for the controlled release of drugs are well known in the art. A common structure employed involves a polymer film or layer surrounding a reservoir containing a drug which may be in the form of a solution or dispersed in a matrix material. The drug diffuses through the polymer film at a controlled rate over a period of time. Many of the prior art devices and systems are said to release the drug at a rate which does not vary with time (see, for example, Higuchi, et al. U.S. Pat. No. 3,710,795 and Baker, et al. U.S. Pat. No. 3,926,188). A wide variety of polymeric materials have been employed in these drug release devices. Baker, et al. U.S. Pat. No. 3,926,188; Zaffaroni U.S. Pat. Nos. 3,993,072 and 3,996,934 and Roseman, et al. 4,308,867 disclose a number of homopolymers, including poly(-dimethyl siloxane) and polyurethane, which may be employed individually as the rate controlling means. Arnold U.S. Pat. Nos. 3,961,628 and Zaffaroni 3,993,072 disclose the use of a diffusive medium in the pores of a microporous polymer to control the release of a drug from an inner reservoir. The diffusive medium is permeable to the passage of the drug and is a liquid, a gel, a colloidal suspension or a sol in which the drug has limited solubility. Specific block copolymers have been taught as the rate controlling means in drug release systems. Fildes, et al. U.S. Pat. No. 4,235,988 discloses the use of a linear block copolymer of polyurethane and polyoxyalkylene while Wong U.S. Pat. No. 4,286,587 discloses the use of block copolymer of styrene and butadiene in this service.

Many different types of drugs may be controllably released by means of the prior art systems. The devices disclosed in the Roseman, et al. patent are said to be particularly adapted for lipophilic pharmacological agents. Although the drugs useful in the polymeric devices of the Zaffaroni U.S. Pat. No. '072 are not categorized by their lipophilic or hydrophilic properties but on their particular activity, viz , hypnotics and sedatives, tranquilizers, anticonvulsants, muscle relaxants, hormonal agents, antiparasitic agents, neoplastic agents, etc., the specifically enumerated drugs which can be administered by the disclosed system include primidone and dapsone.

The prior art delivery systems are disclosed as being capable of delivering from 25 nanograms to 25 grams of drug per day (Zaffaroni U.S. Pat. No. '072) as well as 1 to 1.5 grams per day (Leeper, et al. U.S. Pat. No. 3,938,515). Further, the prior art provides formulae and design parameters so that a device employing specific polymers and materials can be designed to provide a desired rate of release of a given drug (see, for example, the Baker, et al. patent and the Leeper, et al. patent). The graphs in the Baker, et al. patent presenting the drug release rate vs. time clearly show that the initial release of drug is substantially higher than that evidenced a short time later. Although this so-called "burst effect" may be considerable or may occasion some unnecessary side-effect, the prior art fails to disclose or suggest that this initial burst effect may be significantly reduced or eliminated.

It is an object of this invention to provide a polymeric device capable of releasing drugs, particularly lipophilic drugs, at a high, sustained, and preferably zero-order, rate for a prolonged period of time.

It is another object of this invention to provide a rate-controlled drug release system which will eliminate or significantly reduce the initial burst effect of drug release, particularly when employed with lipophilic drugs.

It is a further object of this invention to provide a drug release system capable of zero-order rate release of lipophilic drugs, especially phenytoin, primidone and dapsone.

The achievement of these and other objects will be apparent from the following description of the subject invention.

SUMMARY OF THE INVENTION

In accordance with the present invention, it has been found that significant improvements can be obtained in drug release polymeric devices employing lipophilic drugs wherein the polymeric membrane is composed of a block copolymer of poly(ether-urethane) and poly(-dimethyl siloxane).

In particular, this invention relates to an improvement in a drug release device for the continuous and controlled administration of a drug over a prolonged period of time, said device comprising a reservoir containing the drug in a pharmaceutically acceptable carrier and a medically acceptable, outer polymeric membrane surrounding said reservoir, said polymeric membrane being formed of a drug release rate-controlling material which is permeable to the passage of said drug by diffusion, said improvement comprising:

(a) forming said membrane from a block copolymer of poly(ether-urethane) and poly(dimethyl siloxane) and (b) employing as the drug a lipophilic drug having a structural molecular weight below about 1000.

DESCRIPTION OF THE PREFERRED EMBODIMENTS

Figure 1:
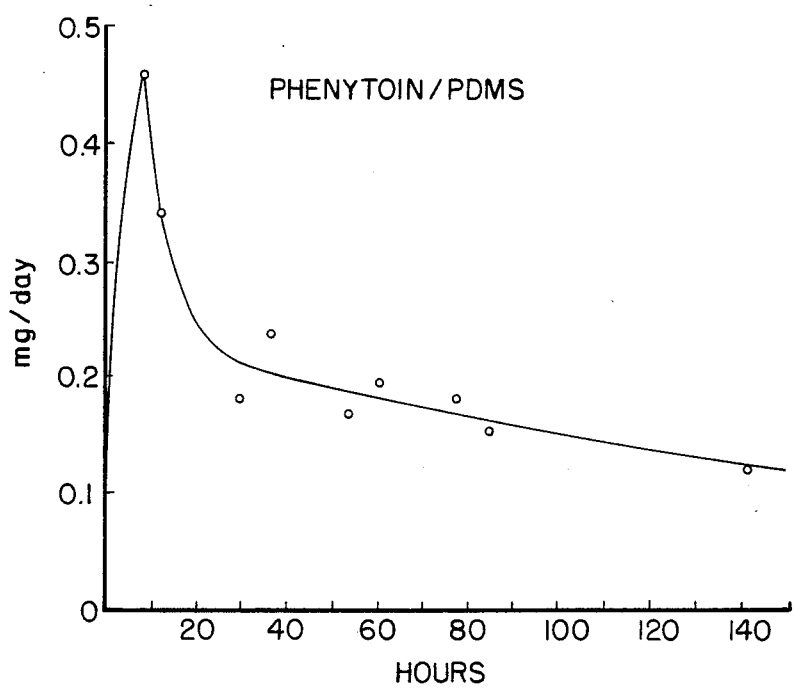
FIG. 1 is a graph showing the permeation of phenytoin through poly(dimethyl siloxane) at 37° C.
Figure 2:
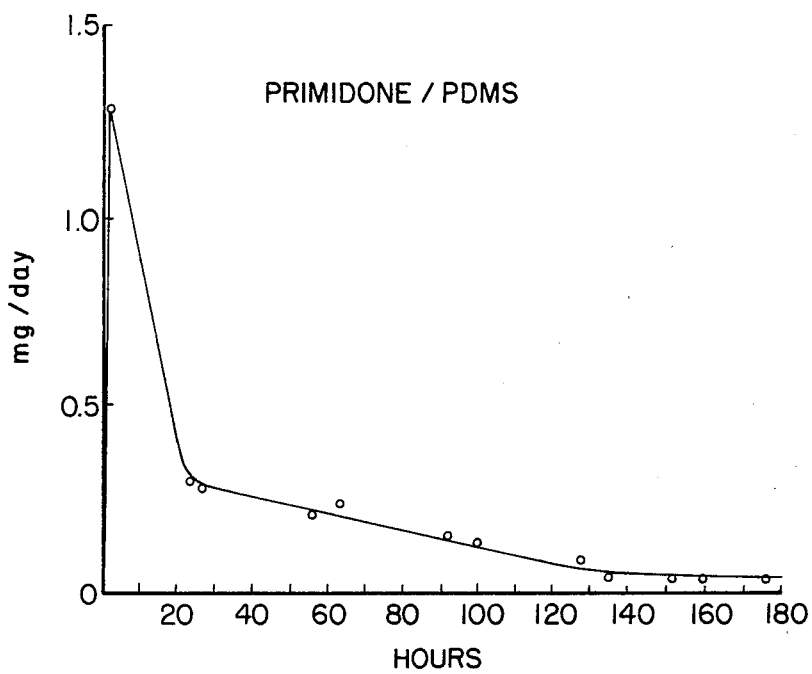
FIG. 2 is a graph showing the permeation of primidone through poly(dimethyl siloxane) at 37° C.
Figure 3:
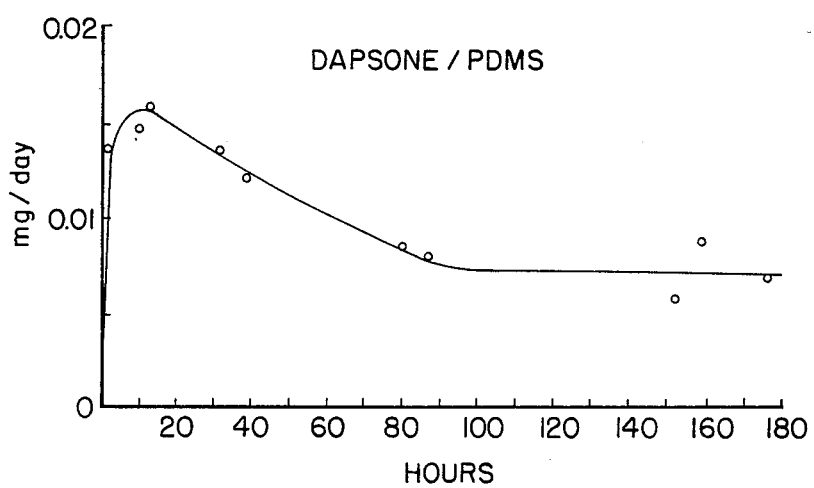
FIG. 3 is a graph showing the permeation of dapsone through poly(dimethyl siloxane) at 37° C.

The present invention relates to a drug release device useful for lipophilic drugs. By employing a block copolymer of poly(ether-urethane) and poly(dimethyl siloxane) as the polymeric membrane controlling the release of the drug, not only can exceptionally high dosage rates be obtained at a zero-order rate of release over a prolonged period time, but the high initial burst effect of drug release observed with prior art devices can be eliminated or at least substantially reduced.

The copolymer employed in the devices of this invention is a poly(ether-urethane)/poly(dimethyl siloxane) block copolymer. The term "segmented" copolymer is also employed in the art in describing these copolymers. The polyurethane portion of the copolymer has been designated as the ether type to distinguish it from polyurethanes of the ester type. The ether type of polyurethane is the more commonly used in medical applications. The block copolymer employed here must, of course, be medically acceptable since these devices can be employed in dispensing drugs to human beings or non-human animals. The preferred block copolymers are known materials and have been used heretofore in medical implants and in various cardiovascular devices. Particularly preferred poly(ether-urethane)/poly(dimethyl siloxane) block copolymers are commercially, available under the trademark Cardiothane ® and Avcothane ®. As especially useful copolymer is designated under the trademarks Avcothane-51 ® where the polymers are in the weight ratio of poly(ether-urethane) to poly(dimethyl siloxane) of 90:10. Polymer weight ratios ranging to about 70:30 are also useful. When these copolymers are cured, the silane portion becomes cross-linked providing an extremely stable polymeric material.

The useful block copolymers have a permeability which permits their use in rate-controlled drug release devices. To enhance this permeability, it has been found that a solvent pre-treatment is particularly useful. A solvent mixture of ethylene glycol and a $C_2$–$C_3$ alcohol will effectively provide the block copolymer with the desired permeability. The copolymer is immersed in the solvent mixture for a period of time effective to provide the permeability desired. A period of 5–30 minutes is usually adequate when employing a solvent mixture of 1:1 volume ratio. The volume ratio of glycol to alcohol may range from 2:8 to 8:2. A mixture of ethylene glycol and ethyl alcohol is preferred although n-propyl alcohol or isopropanol may be substituted for the ethyl alcohol.

The block copolymer devices of the invention provide controlled release of a drug for prolonged periods when used with lipophilic drugs. Since effective results are not obtained with high molecular weight materials such as hormones, the lipophilic drugs dispensed with the instant devices should be limited to those having structural molecular weights below about 1000. Lipophilic drugs having molecular weights of about 200 to about 300 work especially well in these devices. Several drugs were particularly well dispensed with the block copolymer devices of this invention—phenytoin (diphenyl hydantoin), primidone (a congener of phenobarbital) and dapsone (a sulfone antimicrobial agent). Phenytoin and primidone are the primary drugs employed in the treatment of epileptic seizures and related convulsive disorders, whereas dapsone is a widely used drug in the treatment of leprosy and to a lesser extent in dermatitis herpetiformis. The constant rate of release of these primary drugs used in the treatment of epilepsies and relative convulsive disorders, as well as leprosy and other microbial skin diseases, will be found useful in transdermal and/or transmucosal application, thus avoiding the necessity of frequent therapies by oral ingestion of tablets and other parenteral drug administrations for the prophylaxis or chronic therapies of the above-mentioned diseases. This can be especially significant because epileptic disorders are particularly characteristic in children, whereas leprosy is predominant in certain underdeveloped countries. However, the drug release system is not limited to the treatment of these diseases and may be used with the lipophilic drugs described above for the treatment of a wide variety of disorders and diseases.

These drug release devices are constructed with the block copolymer formed in a polymeric membrane surrounding a reservoir containing the lipophilic drug to be administered. The drug is conveniently provided in the form of a saturated or supersaturated solution of the lipophilic drug in a medically acceptable solvent. The configuration of the polymer membrane is dictated by the end use and therefore may be provided in a variety of shapes and sizes. The thickness of the polymeric membrane will also be dependent on several factors including, for example, the particular drug being dispensed, the required dosage rate, the period of treatment and the permeability of the membrane. Design procedures for these devices are well known in the art as pointed out hereinbefore.

The devices of this invention may be administered to humans and to non-human animals. The dispensing of lipophilic drugs by means of these devices may be effected transdermally or transmucosally. In addition, the device may be implanted subcutaneously and refilled with a syringe by procedures known in the art. The devices may be implanted surgically and removed in the same fashion.

In a preferred embodiment of this invention, a second polymeric membrane is interposed between the drug reservoir and the outer polymeric membrane of the block copolymers. This device provides improved regulation of the dispensing of the lipophilic drug as compared to the device without the second polymeric membrane. Although both membranes are permeable permitting the drug to pass therethrough, the rate of diffusion of the drug through the second polymeric membrane per unit area of polymeric membrane cross-sectional flow path per unit of polymeric membrane thickness is less than the rate of diffusion of the drug through the outer polymeric membrane per unit area of polymeric membrane cross-sectional flow path per unit of polymeric thickness. In this fashion, the second polymeric membrane is made the dosage controlling means while the outer polymeric membrane is made the rate controlling means.

The second polymeric membrane is composed of a medically acceptable, inert, microporous polymer material with a different polymeric material filling the micropores. This polymeric material filling the micropores provides the same function as the outer polymeric membrane in that it is permeable to the passage of the drug by diffusion and may be essentially the same material constituting the outer polymeric membrane.

The microporous polymer material has a plurality of micropores having a pore size of about 1 nm to about 100 μm. Typically, this porous polymer may be composed of polyethylene, polypropylene, polysulfone, polycarbonate, nitrocellulose and the like.

The micropores of the polymer may be filled with the permeable material by either of two processes well known in the art—a solvent coating process or a glow surface of the balloon material which corresponds to its actual clinical use.

Results

Figure 4:
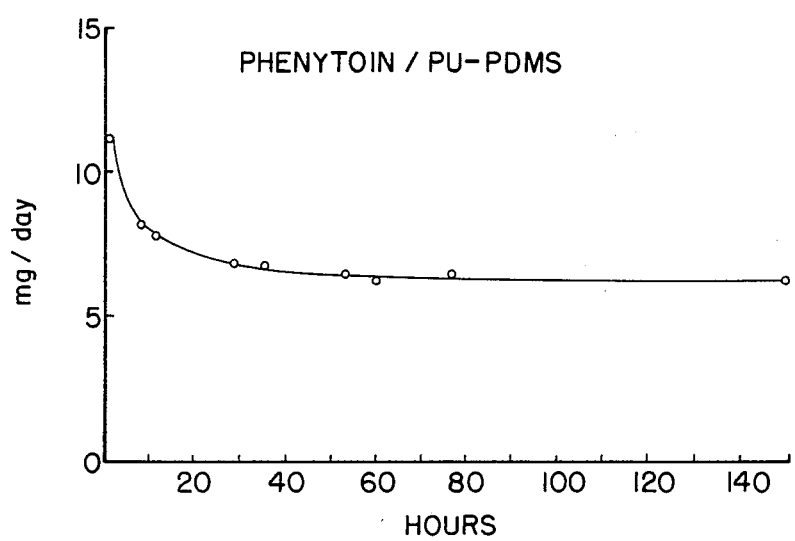
FIG. 4 is a graph showing the permeation of phenytoin through poly(ether-urethane)/poly(dimethyl siloxane) block copolymer at 37° C.
Figure 5:
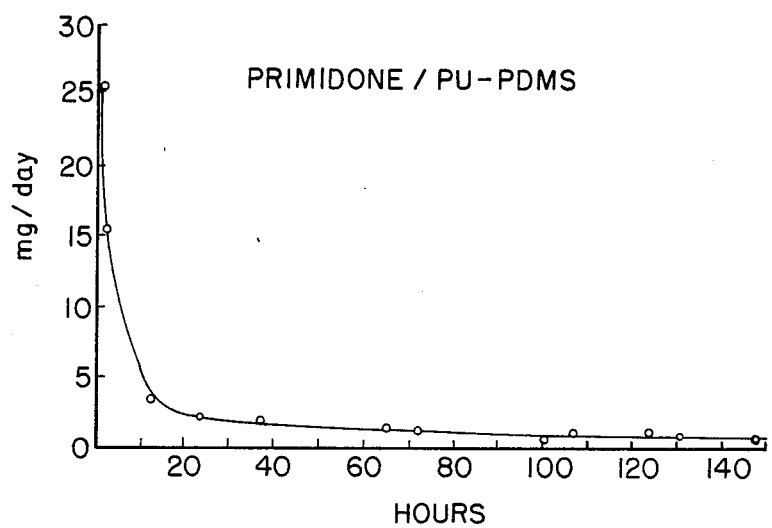
FIG. 5 is a graph showing the permeation of primidone through poly(ether-urethane)/poly(dimethyl siloxane) block copolymer at 37° C.
Figure 6:
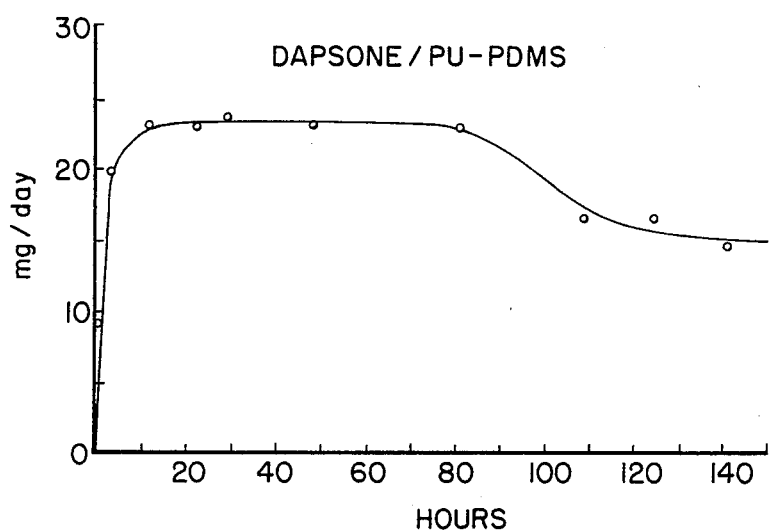
FIG. 6 is a graph showing the permeation of dapsone through poly(ether-urethane)/poly(dimethyl siloxane) block copolymer at 37° C.

The rates of permeation (in milligram/day) of phenytoin, primidone and dapsone through the silica-filled poly(dimethyl siloxane) and the block copolymer of poly(etherurethane) and poly(dimethyl siloxane) are shown in FIGS. 1-6. In the case of poly(dimethyl siloxane), there is a very large burst effect, followed by an exponential first-order decrease of drug transport. The burst effect is especially pronounced with phenytoin (FIG. 1) and primidone (FIG. 2), but somewhat lesser with dapsone (FIG. 3) which showed also a leveling out at about 100 h with constant release rates up to 180 h. In the case of the poly(ether-urethane)/poly(dimethyl siloxane) block copolymer, the situation was quite different. First, this polymer exhibited far greater permeabilities to the three drugs than the poly(dimethyl siloxane), as seen in FIGS. 4-6. Second, burst effects were only observed with phenytoin and primidone, but this effect was significantly less with the former drug. Third, essentially constant rate (zero-order) kinetics was observed with phenytoin between 29 and 149 h. Fourth, with dapsone there was no burst effect and constant rate release was observed between 12 to 80 h, followed by only a relatively moderate decrease in drug transport up to the conclusion of the experiment of 141 h.

The normalized fluxes ($\mu$g-mm/cm$^2$-day) are summarized in Table 1 for the drugs and the two polymers with specified time periods indicated in parentheses. As can be seen, the permeability of the poly(ether-urethane)/poly(dimethyl siloxane) block copolymer is much greater than that of the poly(dimethyl siloxane) homopolymer.

The diffusion constants calculated from initial desorption data at 37° C.±0.15 for the three drugs through the poly(ether-urethane)/poly(dimethyl siloxane) block copolymer are as follows: phenytoin=$8.6 \times 10^{-9}$ cm$^2$/s; primidone=$2.8 \times 10^{-9}$ cm$^2$/s; dapsone=$2.4 \times 10^{-8}$ cm$^2$/s. The diffusion constants were not obtained with the poly(dimethyl siloxane) homopolymer due to the much smaller amount of drugs transported through the membranes resulting in greatly diminished drug release in desorption experiments, thus making the ultraviolet determinations even with the sensitive spectrophotometer unreliable.

Since phenytoin as well as primidone are widely used drugs in the treatment of all types of epilepsies and convulsive disorders except absence seizures, the observed constant drug release rate of phenytoin through the poly(ether-urethane)/poly(dimethyl siloxane) block copolymer with only a relatively moderate initial burst effect may be useful in certain types of controlled drug delivery systems. Similarly, since the sulfone antibacterial drug, dapsone, is widely used in the treatment of leprosy and to some extent also in dermatitis herpetiformis (Duhring's Disease), the lack of burst effect and constant (zero-order) kinetics at least up to 80 h may find usefulness in rate-controlled drug release systems.

TABLE 1

Normalized flux for phenytoin, primidone and dapsone through poly(dimethyl siloxane) (PDMS) and poly(ether-urethane)/poly(dimethyl siloxane) (PU—PDMS) block copolymer at 37° C.

| Polymer | Drug | Normalized flux ($\mu$g-mm/cm$^2$-day) | Comments |
|---|---|---|---|
| PDMS | Phenytoin | 12.0 (between 30-120 h) | Large burst effect with exponential decrease |
| PDMS | Primidone | 9.5 (between 24-176 h) | |
| PDMS | Dapsone | 0.8 (between 10-87 h) | Large burst effect with exponential decrease until approx. 100 h; followed by constant rate until 180 h |
| PDMS | Dapsone | 0.5 (between 87-176 h) | |
| PDMS | Dapsone | 0.7 (between 10-176 h) | |
| PU—PDMS | Phenytoin | 552 (between 29-149 h) | Constant rate |
| PU—PDMS | Phenytoin | 626 (between 2-149 h) | |
| PU—PDMS | Primidone | 106 (between 65-131 h) | |
| PU—PDMS | Primidone | 140 (between 13-148 h) | |
| PU—PDMS | Dapsone | 1962 (between 12-81 h) | Constant rate; no burst effect |
| PU—PDMS | Dapsone | 1733 (between 3-141 h) | |

What is claimed is:

1. In a drug release device for the continuous and controlled administration of a drug over a prolonged period of time, said device comprising a reservoir containing the drug in a pharmaceutically acceptable carrier and a medically acceptable, outer polymeric membrane surrounding said reservoir, said polymeric membrane being formed of a drug release rate-controlling material which is permeable to the passage of said drug by diffusion, the improvement which comprises:
   (a) forming said membrane from a block copolymer of poly(ether-urethane) and poly(dimethyl siloxane) and
   (b) employing as the drug a lipophilic drug having a structural molecular weight below about 1000.

2. The improvement according to claim 1 wherein said block copolymer is pre-treated with a solvent mixture of ethylene glycol and a $C_{2-3}$ alcohol for a period of time effective to increase the permeability of said block copolymer.

3. The improvement according to claim 2 wherein the $C_{2-3}$ alcohol is ethyl alcohol.

4. The improvement according to claim 3 wherein the solvent mixture is a 1:1 volume mixture.

5. The improvement according to claim 2 wherein the $C_{2-3}$ alcohol is n-propyl alcohol.

6. The improvement according to claim 2 wherein the $C_{2-3}$ alcohol is isopropyl alcohol.

7. The improvement according to claim 1 wherein the reservoir contains a saturated solution of the lipophilic drug in a pharmaceutically acceptable solvent.

8. The improvement according to claim 7 wherein the solution is supersaturated.

9. The improvement according to claim 1 wherein the lipophilic drug is phenytoin.

10. The improvement according to claim 1 wherein the lipophilic drug is primidone.

11. The improvement according to claim 1 wherein the lipophilic drug is dapsone.

12. The improvement according to claim 1 wherein the device additionally comprises a second polymeric discharge process. A closely related process, plasma polymerization, polymerization may be used instead of glow discharge polymerization where its use would be advantageous.

In the solvent coating process, a pre-polymer of the poly(ether-urethane)/poly(dimethyl siloxane) block copolymer may be employed. In its pre-polymer condition, the block copolymer has not been cured and thus is more readily soluble since cross-linking has not taken place. The pre-polymer is dissolved in a solvent such as a 2:1 mixture of tetrahydrofuran and dioxane, and this solution is employed to coat a film of the copolymer on the microporous polymer. The solvent is slowly evaporated under ambient conditions thereby forming a copolymer film on the microporous polymer and filling the micropores with the copolymer. The block copolymer may then be cured by known procedures with or without the use of a catalyst such as a peroxide, and the like. In this fashion, the copolymer filling the pores is essentially the same as the block copolymer of the outer polymeric membrane.

In circumstances where the copolymer formed in the micropores by the solvent coating process has too much permeability for the intended use, subjecting it to glow discharge in the presence of an inert gas atmosphere has been found to decrease the permeability.

In the well known glow discharge polymerization process, two or more monomers are exposed to a glow discharge in the presence of a film of the microporous polymer. The monomers copolymerize forming a film on the microporous polymer which fills the micropores. By careful selection of the monomers and the glow discharge conditions, the desired degree of permeability can be obtained. Useful monomers include hexamethyl disiloxane, and the like as one monomer and ethylene, allene, allylamine, and the like as the other monomer or monomers. Although the copolymer obtained in the glow discharge process is not the block copolymer of the outer polymeric membrane, it has a permeability which makes it especially useful in these drug release devices.

The following example illustrates the practice of this invention and, in particular, presents a comparison between the drug releasing properties of the block copolymer employed in the devices of the invention and poly(dimethyl siloxane) employed in prior art devices.

Materials

Phenytoin (5,5'-diphenyl hydantoin), reagent grade, dapsone (4,4'-diaminodiphenylsulfone), reagent grade, were obtained from Nakarai Chemicals, Ltd., and primidone (2-desoxyphenobarbital), pharmaceutical grade, from Dainippon Seiyaku Co. Silica-filled poly(dimethyl siloxane) (Dow Corning Silastic ® 500-1) actual measured average thickness of 0.170 mm, and a poly(ether-urethane)/poly(dimethyl siloxane) block copolymer (Cardiothane ®, Avcothane ®) with measured average thickness of 0.212 mm, were used in the permeability experiments. This latter block copolymer was taken directly from unused intra-aortic balloons, as further discussed below. The solvents (ethyl alcohol, ethylene glycol) were freshly distilled.

Apparatus

The experimental set-up consisted of a stoppered two-compartment permeability cell, each compartment capable of holding 40 ml solution. The polymer membrane under investigation was positioned between two O-rings and held there with a clamp mechanism. The effective diameter for drug penetration of the polymer membranes positioned between the two compartments of the permeability cell was 17.8 mm. The permeability cell was placed in a constant temperature bath, controlled by a magnetic contact thermoregulator at 37° C.±0.15, and each compartment was equipped with a magnetic stirrer bar. One of the compartments contained 40 ml of the saturated solution of the drug in freshly distilled ethylene glycol/ethyl alcohol (50:50 volume %), whereas the other compartment, filled with 40 ml of the same solvent, served as the sampling cell. Aliquots (1 ml) taken from this cell were replaced by equal quantities of pure solvent. Prior to the permeation experiments, ultraviolet spectra of the three drugs were obtained on a Shimadzu Multipurpose (double beam) Recording Spectrophotometer, Model MPS-50L. Ultraviolet calibration curves at the selected wave lengths were obtained with a sensitive Shimadzu Double Beam Spectrophotometer, Model U.V. 210A with digital readout. The following absorption peaks were used for calibration purposes and for the permeability measurements: phenytoin at 259 nm; primidone at 259 nm; dapsone at 299 nm. The data of drug release through the polymer membranes were subjected to least square analyses with the aid of an NEC microcomputer.

Diffusion constants were calculated from initial desorption data using Fick's second law of diffusion: $M_t/M_\infty = 4(Dt/\pi l^2)^{\frac{1}{2}}$, where $M_t$=drug desorbed after time, t; $M_\infty$ =total drug desorbed; l=thickness of the polymer film, and t=time. In the sorption-desorption method for the calculation of the diffusion constants, films of the polymers used for the permeability studies were immersed in saturated solutions of the drugs in ethylene glycol:ethyl alcohol (50:50 volume %) at 37° C.±0.15 for 72 h. The polymer films were removed from the saturated drug solutions, rinsed rapidly with the solvent to remove any adhering drug solution to the surface, and then the polymer films were placed in 40 ml of the pure solvent. The rates of desorption of the drugs were measured spectrophotometrically at the wave length mentioned above, by taking aliquots (1 ml) at 15-min intervals (and replacing these with fresh solvent) up to 3 h. The diffusion constants were calculated from the initial desorption data (as required by theory) of up to approximately 90 min. The normalized fluxes ($\mu$g-mm/cm$^2$-day) were calculated from permeability data.

Both the poly(dimethyl siloxane) and the poly(etherurethane)/poly(dimethyl siloxane) block copolymer were thoroughly cleaned with distilled water and treated for 15 min in the permeation medium (ethylene glycol:ethyl alcohol, 50:50 volume %). In the case of the block copolymer, sections of unused intra-aortic balloon were placed in the permeability cell in such a way that the outside (usually blood-contacting) smooth surface served as the entrance point for the drugs under investigation, whereas the inside surface projected toward the exit cell. In other words, the outside, smooth surface was the one exposed to the saturated drug solution. The reason for this was that the molecular architecture of the outside and inside surfaces are known to differ in important respects and the film is anisotropic. The solvent pretreatment further enhanced this property. Therefore, it was important to study the permeability of this block copolymer by maintaining the permeation gradient from the blood-contacting (outside)

membrane interposed between the outer polymeric membrane and the drug reservoir, said second polymeric membrane comprising a medically acceptable, inert, microporous polymeric material having a plurality of micropores with a pore size of about 1 nm to about 100 μm, and a medically acceptable drug release rate controlling material which is permeable to the passage of said drug by diffusion housed in the micropores, the rate of diffusion of the drug through the second polymeric membrane per unit area of polymeric membrane cross-sectional flow path per unit of polymeric membrane thickness is less than the rate of diffusion of the drug through the outer polymeric membrane per unit area of polymeric membrane cross-sectional flow path per unit of polymeric membrane thickness.

13. The improvement according to claim 12 wherein the material in the micropores is a copolymer of poly(etherurethane) and poly(dimethyl siloxane).

14. The improvement according to claim 13 wherein the copolymer is formed in the micropores by a solvent coating process of a block copolymer of said copolymer followed by a cross-linking process to form the cross-linked copolymer.

15. The improvement according to claim 12 wherein the material in the micropores is a copolymer formed in the micropores by a glow discharge polymerization process.

16. The improvement according to claim 15 wherein the copolymer comprises hexamethyl disiloxane as one monomer and ethylene, allene or allylamine as a second monomer.

* * * * *